(12) United States Patent
Smith et al.

(10) Patent No.: US 10,076,600 B2
(45) Date of Patent: Sep. 18, 2018

(54) TARGETED APHERESIS FOR THE TREATMENT OF RHEUMATOID ARTHRITIS AND IMMUNE DISORDERS

(71) Applicants: Henry J. Smith, Temecula, CA (US); James R. Smith, Laguna Niguel, CA (US)

(72) Inventors: Henry J. Smith, Temecula, CA (US); James R. Smith, Laguna Niguel, CA (US)

(*) Notice: Subject to any disclaimer, the term of this patent is extended or adjusted under 35 U.S.C. 154(b) by 148 days.

(21) Appl. No.: 14/978,910

(22) Filed: Dec. 22, 2015

(65) Prior Publication Data

US 2016/0106905 A1    Apr. 21, 2016

Related U.S. Application Data

(63) Continuation of application No. 13/507,566, filed on Jul. 11, 2012, now abandoned.

(51) Int. Cl.

| *B01D 15/38* | (2006.01) |
|---|---|
| *A61M 1/36* | (2006.01) |
| *C07K 16/46* | (2006.01) |
| *A61K 39/39* | (2006.01) |

(Continued)

(52) U.S. Cl.
CPC .......... *A61M 1/362* (2014.02); *A61M 1/3486* (2014.02); *B01D 15/00* (2013.01); *B01D 15/3804* (2013.01); *B01D 15/3809* (2013.01); *A61M 1/3679* (2013.01)

(58) Field of Classification Search
CPC ........ B01D 15/00; B01D 15/26; B01D 29/56; B01D 29/58; B01D 36/00; B01D 2215/00; B01D 15/3809; B01D 15/3804; C07K 16/18; C07K 16/34; C07K 16/42; C07K 16/44; C07K 16/46; C07K 16/468; A61M 1/36; A61M 1/3679; A61M 1/3689; A61M 1/38; A61M 1/362; A61M 1/3486; A61K 39/395; A61K 39/44; A61K 39/3956; A61K 2039/505; A61K 2039/507
USPC .... 210/263, 266, 335, 638, 645, 660, 502.1; 424/134.1, 140.1, 141.1, 142.1, 143.1; 604/406, 6.01, 6.09; 514/16.6, 861, 867, 514/868; 530/412, 413, 415, 387.1, 530/387.2, 388.15, 388.2
See application file for complete search history.

(56) References Cited

U.S. PATENT DOCUMENTS

| 3,959,251 A | * | 5/1976 | Porath | C08B 37/0039 435/178 |
|---|---|---|---|---|
| 4,153,417 A | * | 5/1979 | Hallgren | G01N 33/564 435/7.92 |

(Continued)

*Primary Examiner* — Joseph Drodge
(74) *Attorney, Agent, or Firm* — Stetina Brunda Garred & Brucker

(57) ABSTRACT

This invention uses "Targeted Apheresis" to treat patients with Rheumatoid Arthritis and other autoimmune and inflammatory disorders. "Targeted Apheresis" is a process whereby only the pathogenic and pro-inflammatory elements associated with the disease symptoms are simultaneously and selectively removed from the blood by passing the blood through an extracorporeal affinity device containing selective binding agents. Removal of these pathogenic and pro-inflammatory elements will ameliorate the symptoms of autoimmune disease and may prolong the period of disease remission.

20 Claims, 1 Drawing Sheet

(51) Int. Cl.
*A61M 1/34* (2006.01)
*B01D 15/00* (2006.01)

(56) References Cited

U.S. PATENT DOCUMENTS

| | | | | |
|---|---|---|---|---|
| 4,432,871 A * | 2/1984 | Yamawaki | ........... | A61M 1/3679 |
| | | | | 210/195.1 |
| 4,863,611 A * | 9/1989 | Bernstein | ........... | A61M 1/3675 |
| | | | | 210/196 |
| 5,258,503 A * | 11/1993 | Yokohari | ........... | A61M 1/3679 |
| | | | | 210/502.1 |
| 5,782,792 A * | 7/1998 | Jones | ................ | A61M 1/3472 |
| | | | | 210/195.2 |
| 5,817,528 A * | 10/1998 | Bohm | .................... | A61K 35/14 |
| | | | | 435/174 |
| 6,498,007 B1 * | 12/2002 | Adachi | .................. | A61K 35/14 |
| | | | | 435/5 |
| 6,551,266 B1 * | 4/2003 | Davis, Jr. | ........... | A61M 1/3413 |
| | | | | 604/6.09 |
| 6,713,252 B2 * | 3/2004 | Sawada | ............... | A61M 1/3679 |
| | | | | 424/140.1 |
| 6,866,846 B1 * | 3/2005 | Heinrich | ............ | A61M 1/3679 |
| | | | | 424/140.1 |
| 7,267,771 B2 * | 9/2007 | Gorsuch | ............ | A61M 1/1678 |
| | | | | 210/321.69 |
| 2004/0213781 A1 * | 10/2004 | Hogarth | ........... | C07K 14/70535 |
| | | | | 424/143.1 |
| 2006/0159680 A1 * | 7/2006 | Smith | ................. | A61M 1/3679 |
| | | | | 424/140.1 |
| 2008/0160036 A1 * | 7/2008 | Chen | .................. | A61K 38/1709 |
| | | | | 424/179.1 |
| 2008/0314817 A1 * | 12/2008 | Fujita | .................. | A61M 1/3627 |
| | | | | 210/263 |
| 2009/0148447 A1 * | 6/2009 | Ledbetter | ........... | C07K 16/2803 |
| | | | | 424/134.1 |
| 2011/0097344 A1 * | 4/2011 | Darashkevich | ...... | C07K 16/065 |
| | | | | 424/176.1 |
| 2012/0323158 A1 * | 12/2012 | Tebbey | ................ | A61M 1/3472 |
| | | | | 604/6.01 |
| 2013/0039925 A1 * | 2/2013 | Bansal | .................. | C07K 16/18 |
| | | | | 424/158.1 |
| 2013/0131423 A1 * | 5/2013 | Wang | .................. | A61M 1/3621 |
| | | | | 600/1 |
| 2013/0209476 A1 * | 8/2013 | Brenner | ............ | A61K 31/7088 |
| | | | | 424/141.1 |

* cited by examiner

TARGETED APHERESIS FOR THE TREATMENT OF RHEUMATOID ARTHRITIS AND IMMUNE DISORDERS

CROSS-REFERENCE TO RELATED APPLICATIONS

This present application claims priority to provisional patent application No. 61/574,585 filed on Aug. 5, 2011 titled "Targeted Apheresis for the Treatment of Rheumatoid Arthritis and Immune Disorders".

STATEMENT RE: FEDERALLY SPONSORED RESEARCH/DEVELOPMENT

Not Applicable

BACKGROUND

The main application of this invention is in the treatment of autoimmune diseases such as rheumatoid arthritis and other inflammatory conditions using a process of "Targeted Apheresis".

Current methods of treatment of autoimmune disease typically consist of: for mild cases of autoimmune disease treatment usually consists of aspirin or non-steroidal anti-inflammatory drugs. For more severe cases steroidal drugs such as cortisone, prednisone and methylprednisolone are used. Finally, in cases where the patients become unresponsive to these drugs more cytotoxic drugs such as methotrexate and/or immune modulating drugs may be used. In addition to their therapeutic effect these drugs all have a systemic effect and can cause serious side-reactions. It is desirable to have a treatment process that has fewer side effects.

Apheresis is a process where the patient's blood is passed through an extracorporeal device that physically removes the pathogenic substances that are causing the disease symptoms. As apheresis does not involve administering pharmaceuticals there is no adverse systemic effect on the patient. Apheresis is not a cure for the disease; rather it is a treatment modality that can remove certain of the pathogenic compounds that are contributing to the symptoms of the disease and therefore ameliorate disease symptoms for a period of time.

The principle and practice of using apheresis to treat autoimmune disease is well-established. Therapeutic apheresis has been used to treat a variety of autoimmune diseases and immune disorders including: Rheumatoid Arthritis (RA), Systemic Lupus Erythematosus (SLE), Myasthenia Gravis (MG), Guillain-Barre Syndrome, Goodpasture's Syndrome, and Idiopathic Thrombocytopenic Purpura. The conventional method of performing therapeutic apheresis however is very limited and inefficient. For example, current apheresis therapy uses a single process to treat a variety of autoimmune diseases by removing IgG immunoglobulins in a non-specific fashion. This process is inefficient because a large amount of native IgG is removed along with the pathological IgG autoantibodies involved in the autoimmune disease process. Moreover, removing native IgG may stress the patient and increase susceptibility to infection.

Rheumatoid arthritis patients have "altered IgG" in which "hidden" regions of the IgG molecule are exposed. They produce rheumatoid factor (RF) which is an IgM autoantibody that reacts with the altered IgG. This can result in the formation of immune complexes that can deposit in joints, organs and tissues to cause the symptoms of arthritis.

Rheumatoid arthritis patients may also produce IgG class and IgA class RF autoantibodies that can also react with "altered IgG" and cause disease symptoms.

Until recently, there was only one approved apheresis method in the US for treating rheumatoid arthritis.-the Prosorba® Column. The Prosorba® column is an immunosorbent device that contains Protein A covalently bound to inert silica granules. When plasma is passed thru the device the immobilized Protein A binds out IgG class immunoglobulins and circulating immune complexes. The cleaned plasma is then returned to the patient. This process however, is inefficient because it removes native IgG along with the altered IgG and immune complexes, and a typical course of treatment required multiple apheresis procedures to achieve a result. Also, it did little to remove the circulating unbound RF autoantibodies that are also involved in the disease process. There was also some controversy as to whether the observed beneficial effect is due to removal of immune complexes, or to the leaching out of small amounts of Protein A and other compounds which are introduced back into the patient. The Prosorba® Column was withdrawn from the market in 2006 because of lack of demand due to the high cost of treatment; and there are currently no FDA approved devices for treating RA using apheresis.

In view of the shortcomings of current apheresis methods for treating RA, it would be desirable to develop an apheresis method that would be more efficient in selectively removing the immune complexes as well as the unbound RF autoantibodies involved in the disease symptoms of rheumatoid arthritis.

It would also be advantageous if some of the elements thought to be responsible for initiating the RA disease process were also removed. For example; it is believed that "altered IgG" is an initiator for the rheumatoid factor immune response. Therefore removal of "altered IgG" using apheresis could suppress or delay initiation of the autoimmune response. It would be desirable to develop an apheresis method for removing "altered IgG".

In addition to the pathogenic elements that are characteristic for a particular autoimmune disease such as rheumatoid factor for rheumatoid arthritis there are also other factors that may contribute and/or exacerbate disease symptoms. For example; patients with autoimmune disease produce pro-inflammatory cytokines such as tumor necrosis factor alpha (TNF-alpha) and Interleukin-1 (IL-1) that may stimulate the autoimmune response and exacerbate disease symptoms. It would be desirable to develop an apheresis method that would remove these pro-inflammatory elements and ameliorate disease symptoms.

This invention teaches a novel comprehensive approach to therapeutic apheresis that employs a method of simultaneously and selectively targeting the removal of only the pathogenic and pro-inflammatory elements involved in the disease process while leaving the normal elements intact. For example, to treat RA this method of "Targeted Apheresis" will remove the pathogenic factors such as RF and immune complexes believed to be directly involved in the disease process; and also remove the pro-inflammatory cytokines such as TNF-alpha and IL-1 that can exacerbate disease symptoms; and also remove factors such as "altered IgG" that can incite the development of the disease process.

The novelty of this invention is the use of a single targeted apheresis affinity device to simultaneously and selectively remove multiple pathogenic and pro-inflammatory factors from the blood of patients with rheumatoid arthritis. The same treatment rationale can be similarly applied to other autoimmune diseases and inflammatory conditions.

BRIEF SUMMARY

This invention describes the treatment of immunological disorders such as rheumatoid arthritis and other inflammatory conditions using "Targeted Apheresis". "Targeted Apheresis" is a process whereby only the pathogenic and pro-inflammatory substances causing the disease symptoms are selectively removed from the blood which is then returned to the individual. For treating RA or other immune diseases a targeted apheresis affinity device containing multiple different immobilized binding agents is employed to selectively remove pathogenic, inflammatory and disease inciting elements from the patient's blood.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
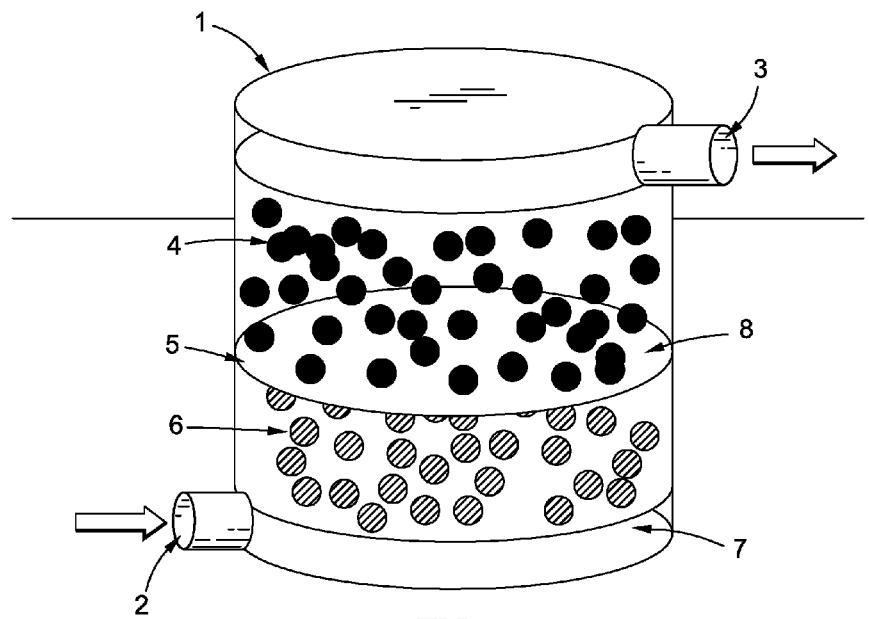
FIG. 1 is a schematic of a targeted affinity device using separate layers of immobilized binding agents.

This invention describes a process of "Targeted Apheresis" that is used to selectively remove rheumatoid factors (RF); immune complexes; pro-inflammatory cytokines; and "altered" IgG from the blood of patients with rheumatoid arthritis. A similar process of targeted apheresis can be employed for treating other immune disorders. This invention is novel in that it describes a comprehensive apheresis process of utilizing multiple binding agents within a single affinity device to selectively remove multiple pathogenic and pro-inflammatory compounds from patients with autoimmune disease and other immune disorders.

Targeted Apheresis for the Treatment of Rheumatoid Arthritis

Patients with active rheumatoid arthritis generally have elevated levels of RF. It is postulated that the arthritis patient for some reason produces "altered" IgG. A common theory is that when the synovium in a joint is damaged certain individuals develop an immune reaction to the damaged proteins. The individual produces an IgG autoantibody that binds to the damaged synovium, and this causes changes in the conformation of the bound IgG autoantibody exposing some previously "hidden regions" within the molecule. The individual's immune system now recognizes the "altered IgG" autoantibody as foreign and produces another autoantibody (rheumatoid factor) against the "altered IgG" molecule. The autoantibody may be of the IgM class antibody (IgM-rheumatoid factor) or the autoantibody may be of the IgG or IgA class antibody. It is generally believed that rheumatoid factor is responsible for disease symptoms by combining with "altered IgG" to form immune complexes that deposit within joints and tissues.

Immunological theory holds that when antibodies bind to antigens an immune complex is formed. The reaction is reversible and all three reactants exist in dynamic equilibrium depending on their relative concentrations. In rheumatoid arthritis the antigen is "altered IgG"; the antibody is "rheumatoid factor"; and the immune complex is "altered IgG bound to rheumatoid factor". It should be noted that although there may be an excess of a particular reactant present at any one time all the reactants are present to some degree in the individual. Therefore this invention teaches that it would be desirable to remove all three reactants to obtain an optimum therapeutic result.

The IgM RF antibody has a total of ten binding sites. Patients with RA generally have circulating RF indicating that there is an excess of circulating RF compared to altered IgG and that not all of the binding sites of the RF molecule are bound to altered IgG. The free binding sites on the RF molecule will be available for binding to immobilized altered IgG within the apheresis affinity device. If IgG or IgA class rheumatoid factor autoantibodies are present they will similarly bind to the immobilized altered IgG within the affinity device.

Patients with arthritis may also have "altered IgG" that can elicit the development of autoimmune rheumatoid factor antibodies. Removal of "altered IgG" using targeted apheresis may ameliorate disease symptoms and/or prolong disease remission.

Patients with RA, and other autoimmune diseases may also have elevated levels of pro-inflammatory cytokines that are thought to participate in exacerbation of disease symptoms. For example; patients with arthritis often have elevated levels of Tumor Necrosis Factor-alpha (TNF-alpha) and Interleukin-1 (IL-1) in the blood. Removal of circulating pro-inflammatory cytokines using targeted apheresis may ameliorate disease symptoms and/or prolong disease remission Affinity Device Components
Preparation of Immobillized Binding Agents:
Preparation of Immobilized "Altered IgG".

Purified IgG can be isolated from human blood and/or from different species of animals and used to prepare the apheresis affinity device. RF has been shown to react with altered IgG from various species of animals. "Altered IgG" can be prepared by either heat-denaturing the purified IgG fraction or by preparing antisera and then allowing the IgG antibodies in the antiserum to bind to antigen thus exposing the "hidden" regions of the antibody molecule.

In the preferred embodiment of this invention heat-denatured human IgG is used in the apheresis affinity device. The IgG is isolated from human blood using standard laboratory methods. For example, human serum is treated with ammonium sulphate to salt out the immunoglobulin fraction which is further purified using gel-filtration, high pressure liquid chromatography and other laboratory methods. Alternatively, the IgG fraction is purified using the Cohn method of purification. These and other methods of purifying IgG are known to those skilled in the art and are within the scope of this invention. The purified IgG is heat-denatured by heating at a temperature between 50 degree C. and 60 degree C. for a period that can range from 12 hours for the lower temperature to 15 minutes for the higher temperature in order to expose the "hidden regions" of the molecule. In the preferred embodiment of this invention the IgG is heat-denatured at 60 degree C. for a period of 15 minutes. Other methods of denaturing the IgG molecule may be employed that are known to those skilled in the art and are within the scope of this invention.

The altered IgG is immobilized by chemically coupling it to an insoluble support matrix such as cross-linked agarose beads. For example, the cross-linked agarose beads are activated using cyanogen bromide and the altered IgG is incubated with the activated agarose to allow coupling to occur. Alternatively, the cross-linked agarose beads are activated using N-hydroxysuccinimide and the altered IgG is coupled to the agarose thru a stable amide bond. There are many different methods of chemically coupling proteins to a variety of insoluble support matrixes. These matrix materials and methods of protein coupling are known to those skilled in the art and are considered within the scope of this invention. The unconjugated material is removed by washing with buffer and the "altered IgG" bound to agarose is used to prepare the affinity device.

Preparation of Immbolized "Altered IgG" Binding Agent.

Patients with RA may have circulating "altered IgG". The altered IgG molecule is believed to be an autoantibody in which the "hidden regions" of the molecule have become exposed and now act as an autoantigen to elicit the production of rheumatoid factor.

Altered IgG can be removed using targeted apheresis employing either immobilized anti-"altered IgG" antibody, or immobilized rheumatoid factor, or immobilized anti-"altered IgG" aptamer.

In one embodiment of this invention the immobilized "altered IgG" binding agent is an antibody. Antibody to the "hidden region" antigen can be prepared in immunized animals injected with purified "altered IgG". The method of immunizing animals to prepare antiserum is well known to those skilled in the art. Alternatively, monoclonal antibodies can be developed against the "hidden region" epitopes. The method of preparing monoclonal antibodies is also well known to those skilled in the art. The polyclonal and monoclonal antibodies can be purified using standard laboratory techniques such as salt-fractionation, gel-filtration and affinity chromatography methods. These and other methods of developing and purifying antibodies are known to those skilled in the art and are within the scope of this invention. In the preferred embodiment of this invention the anti-"altered IgG" monoclonal antibodies are "humanized" by either incorporating human genes into the murine hybridoma or by using fully human hybridomas. The methods of preparing humanized monoclonal antibodies are well known to those skilled in the art and are within the scope of this invention.

Purified anti-"altered IgG" antibody is immobilized by chemically coupling it to an insoluble support matrix such as cross-linked agarose beads. For example, agarose beads are activated using cyanogen bromide or N-hydroxysuccinimide and the antibody is incubated with the activated agarose to allow coupling to occur. There are many different methods of chemically coupling proteins to a variety of insoluble support matrixes. These matrix materials and methods of protein coupling are known to those skilled in the art and are within the scope of this invention. The unconjugated material is removed by washing with buffer and the immobilized anti-"altered IgG" antibody bound agarose is used to prepare the affinity device.

In one embodiment of this invention the "altered IgG" binding agent is human IgM rheumatoid factor obtained from patients with RA. Rheumatoid factor is an autoantibody directed against "altered IgG". Human IgM rheumatoid factor can be purified using standard laboratory techniques such as salt-fractionation, gel-filtration and affinity chromatography methods. These and other methods of purifying RF are known to those skilled in the art and are within the scope of this invention.

Purified RF is immobilized by chemically coupling it to an insoluble support matrix such as cross-linked agarose beads. For example, agarose beads are activated using cyanogen bromide or N-hydroxysuccinimide and the RF is incubated with the activated agarose to allow coupling to occur. There are many different methods of chemically coupling proteins to a variety of insoluble support matrixes. These matrix materials and methods of protein coupling are known to those skilled in the art and are within the scope of this invention. The unconjugated material is removed by washing with buffer and the RF bound agarose is used to prepare the affinity device.

In one embodiment of this invention the "altered IgG" binding agent is an aptamer directed against the "hidden epitope" of the altered IgG molecule. Aptamers are small (i.e., 40 to 100 bases), synthetic oligonucleotides (ssDNA or ssRNA) that can specifically recognize and bind to virtually any kind of target, including ions, whole cells, drugs, toxins, low-molecular-weight ligands, peptides, and proteins. Each aptamer has a unique configuration as a result of the composition of the nucleotide bases in the chain causing the molecule to fold in a particular manner. Because of their folded structure each aptamer will bind selectively to a particular ligand in a manner analogous to an antibody binding to its antigen. Aptamers are usually synthesized from combinatorial oligonucleotide libraries using in vitro selection methods such as the Systematic Evolution of Ligands by Exponential Enrichment (SELEX). This is a technique used for isolating functional synthetic nucleic acids by the in vitro screening of large, random libraries of oligonucleotides using an iterative process of adsorption, recovery, and amplification of the oligonucleotide sequences. The iterative process is carried out under increasingly stringent conditions to achieve an aptamer of high affinity for a particular target ligand such as the "hidden" epitope of the altered IgG molecule.

The aptamer to the "altered IgG" epitope is immobilized by chemically coupling it to an insoluble matrix such as cross-linked agarose beads. For example, agarose beads are activated using cyanogen bromide and the aptamer is incubated with the activated agarose to allow coupling to occur. There are many different methods of chemically coupling aptamers to a variety of insoluble support matrixes. These matrix materials and methods of aptamer coupling are known to those skilled in the art and are within the scope of this invention. The unconjugated material is removed by washing with buffer and the aptamer bound agarose is used to prepare the affinity device.

Preparation of Immonilized TNF-Alpha Binding Agent.

Patients with RA may have circulating TNF-alpha in their blood. TNF-alpha can be removed using apheresis employing either immobilized anti-TNF-alpha antibody or immobilized TNF receptor or immobilized anti-TNF-alpha aptamer.

In one embodiment of this invention the immobilized TNF-alpha binding agent is an antibody. Antibody to TNF-alpha can be prepared in immunized animals injected with purified TNF-alpha. The method of immunizing animals to prepare antiserum is well known to those skilled in the art. Alternatively, monoclonal antibodies can be developed against TNF-alpha epitopes. The method of preparing monoclonal antibodies is also well known to those skilled in the art. The polyclonal and monoclonal antibodies can be purified using standard laboratory techniques such as salt-fractionation, gel-filtration and affinity chromatography methods. These and other methods of developing and purifying antibodies are known to those skilled in the art and are within the scope of this invention.

In the preferred embodiment of this invention the anti-TNF alpha monoclonal antibodies are "humanized" by either incorporating human genes into the murine hybridoma or by using fully human hybridomas. The methods of preparing humanized monoclonal antibodies are well known to those skilled in the art and are within the scope of this invention.

Purified anti-TNF-alpha antibody is immobilized by chemically coupling it to an insoluble support matrix such as cross-linked agarose beads. For example, agarose beads are activated using cyanogen bromide or N-hydroxysuccinimide and the antibody is incubated with the activated agarose to allow coupling to occur. The unconjugated material is removed by washing with buffer and the antibody bound agarose is packed into the targeted apheresis device. There are many different methods of chemically coupling proteins to a variety of insoluble support matrixes. These matrix materials and methods of protein coupling are known to those skilled in the art and are within the scope of this invention.

In another embodiment of this invention the immobilized TNF-alpha binding agent is a tumor necrosis factor receptor protein. Tumor Necrosis Factor Receptor (TNF-R) can be isolated from human cellular extracts and purified using standard laboratory methods. Alternatively, TNF-R can be produced using genetic engineering methods. For example, the genetic code for human TNF-R is cloned using the polymerase chain reaction and attached to plasmid DNA. The altered plasmid DNA is used to transform $E.\ Coli$ bacteria which are grown in fermentation tanks. The transformed bacteria produce human TNF-R which is purified using standard methods such as ion exchange, gel permeation and reverse-phase chromatography. These and other methods of producing recombinant proteins in a variety of expression systems are well known to those skilled in the art and are within the scope of this invention. The recombinant TNF-R may be expressed either complete, or as a fragment which has TNF binding capacity, or as a fusion protein, without affecting the novelty of this invention. In this context, TNF-R refers to either the complete TNF-R moiety, or the binding fragment of TNF-R, or TNF-R as a component of a fusion protein molecule.

Purified TNF-R is immobilized by chemically coupling it to an insoluble support matrix such as cross-linked agarose beads. For example, agarose beads are activated using cyanogen bromide or N-hydroxysuccinimide and the TNF-R protein is incubated with the activated agarose to allow coupling to occur. There are many different methods of chemically coupling proteins to a variety of insoluble support matrixes. These matrix materials and methods of protein coupling are known to those skilled in the art and are considered within the scope of this invention. The unconjugated material is removed by washing with buffer and the TNF-R bound to agarose is used to prepare the affinity device.

In one embodiment of this invention the TNF binding agent is an aptamer directed against the TNF-alpha moiety. Aptamers are small (i.e., 40 to 100 bases), synthetic oligonucleotides (ssDNA or ssRNA) that can specifically recognize and bind to virtually any kind of target, including ions, whole cells, drugs, toxins, low-molecular-weight ligands, peptides, and proteins. Aptamers are usually synthesized from combinatorial oligonucleotide libraries using in vitro selection methods such as the Systematic Evolution of Ligands by Exponential Enrichment (SELEX) using an iterative process of adsorption, recovery, and amplification of the oligonucleotide sequences carried out under increasingly stringent conditions to achieve an aptamer of high affinity for a particular target ligand such as TNF-alpha.

The aptamer to TNF alpha is immobilized by chemically coupling it to an insoluble matrix such as cross-linked agarose beads. For example, agarose beads are activated using cyanogen bromide and the anti-TNF alpha aptamer is incubated with the activated agarose to allow coupling to occur. There are many different methods of chemically coupling aptamers to a variety of insoluble support matrixes. These matrix materials and methods of aptamer coupling are known to those skilled in the art and are within the scope of this invention. The unconjugated material is removed by washing with buffer and the anti-TNF alpha aptamer bound to agarose is used to prepare the affinity device.

Preparation of Immobilized IL-Binding Agent.

Patients with RA may have circulating IL-1 in their blood. IL-1 can be removed using targeted apheresis employing either immobilized anti-IL-1 antibody, or immobilized IL-1 receptor, or immobilized anti-IL-1 aptamer.

In one embodiment of this invention the immobilized IL-1 binding agent is an antibody. Antibody to IL-1 can be prepared in immunized animals injected with purified human IL-1. The method of immunizing animals to prepare antiserum is known to those skilled in the art. Alternatively, monoclonal antibodies can be developed against IL-1 epitopes. The method of preparing monoclonal antibodies is also well known to those skilled in the art and [[are]] is within the scope of this invention. The polyclonal and monoclonal antibodies can be purified using standard laboratory techniques such as salt-fractionation, gel-filtration and affinity chromatography methods. These and other methods of developing and purifying antibodies are known to those skilled in the art and are within the scope of this invention.

In the preferred embodiment of this invention the anti-IL-1 monoclonal antibodies are "humanized" by either incorporating human genes into the murine hybridoma cells or by using fully human:human hybridomas. The methods of preparing humanized monoclonal antibodies are well known to those skilled in the art and are within the scope of this invention.

Purified anti-IL-1 antibody is immobilized by chemically coupling it to an insoluble support matrix such as cross-linked agarose beads. For example, agarose beads are activated using cyanogen bromide or N-hydroxysuccinimide and the anti-IL-1 antibody is incubated with the activated agarose to allow coupling to occur. The unconjugated material is removed by washing with buffer and the antibody bound agarose is packed into the targeted apheresis device. There are many different methods of chemically coupling proteins to a variety of insoluble support matrixes. These matrix materials and methods of protein coupling are known to those skilled in the art and are within the scope of this invention.

In another embodiment of this invention the immobilized IL-1 binding agent is an Interleukin-1 receptor protein. Interleukin-1 receptor (IL-1-R) can be isolated from human cellular extracts and purified using standard laboratory methods. Alternatively, IL-1-R can be produced using genetic engineering methods. For example, the genetic code for human IL-1-R is cloned using the polymerase chain reaction and attached to plasmid DNA. The altered plasmid DNA is used to transform $E.\ Coli$ bacteria which are grown in fermentation tanks. The transformed bacteria produce human IL-1-R which is purified using standard methods such as ion exchange, gel permeation and reverse-phase chromatography. These and other methods of producing recombinant proteins in a variety of expression systems are well known to those skilled in the art and are within the scope of this invention. The recombinant IL-1-R may be expressed either complete, or as a fragment which has IL-1 binding capacity, or as a fusion protein, without affecting the novelty of this invention. In this context, IL-1-R refers to either the complete IL-1-R moiety, or the binding fragment of IL-1-R, or IL-1-R as a component of a fusion protein molecule.

Purified IL-1-R is immobilized by chemically coupling it to an insoluble support matrix such as cross-linked agarose beads. For example, agarose beads are activated using cyanogen bromide or N-hydroxysuccinimide and the IL-1-R protein is incubated with the activated agarose to allow coupling to occur. There are many different methods of chemically coupling proteins to a variety of insoluble support matrixes. These matrix materials and methods of protein coupling are known to those skilled in the art and are considered within the scope of this invention. The unconjugated material is removed by washing with buffer and the IL-1-R bound to agarose is used to prepare the affinity device.

In one embodiment of this invention the IL-1 binding agent is an aptamer directed against the IL-1 moiety. Aptamers are small (i.e., 40 to 100 bases), synthetic oligonucleotides (ssDNA or ssRNA) that can specifically recognize and bind to virtually any kind of target, including ions, whole cells, drugs, toxins, low-molecular-weight ligands, peptides, and proteins. Aptamers are usually synthesized from combinatorial oligonucleotide libraries using in vitro selection methods such as the Systematic Evolution of Ligands by Exponential Enrichment (SELEX) using an iterative process of adsorption, recovery, and amplification of the oligonucleotide sequences carried out under increasingly stringent conditions to achieve an aptamer of high affinity for a particular target ligand such as IL-1.

The aptamer to IL-1 is immobilized by chemically coupling it to an insoluble matrix such as cross-linked agarose beads. For example, agarose beads are activated using cyanogen bromide and the anti-IL-1 aptamer is incubated with the activated agarose to allow coupling to occur. There are many different methods of chemically coupling aptamers to a variety of insoluble support matrixes. These matrix materials and methods of aptamer coupling are known to those skilled in the art and are within the scope of this invention. The unconjugated material is removed by washing with buffer and the anti-IL-1 aptamer bound to agarose is used to prepare the affinity device.

Apheresis Affinity Device

Typically, the affinity device will be constructed as a cylinder with an inlet to allow plasma to enter at one end, and an outlet at the opposite end to allow the cleaned plasma to exit and be returned to the patient. Other device configurations of different shapes and sizes may be designed incorporating the same basic design elements without affecting the novelty of this invention.

The affinity device is constructed of material that is nontoxic and which provides rigid support to the agarose or other insoluble matrix beads within. Typically, the container material will be of a plastic composition such as polystyrene, or polyvinyl, or polypropylene or polycarbonate or other similar material. There is an inside filter at the bottom of the device to contain the agarose beads within the container; and there is also an inside filter at the top of the device to contain the agarose within the container. Typically these filters are composed of porous glass, plastic, or cellulosic material that may be in the form of filter discs and/or filter membranes. These filters will allow thru passage of fluid such as plasma, but not particulate material such as agarose beads. The manufacture of these types of devices and the materials used are known to those skilled in the art and are within the scope of this invention.

In one embodiment of this invention the affinity device will contain two of more layers of agarose beads separated by one or more internal filters (FIG. 1). In the example shown in FIG. 1, the device consists of a rigid container (1) with an inlet orifice (2) and an outlet orifice (3). Within the container there is a layer of agarose beads coated with a binding agent shown in black (4) separated by a porous membrane (5) from a second layer of agarose beads coated with a different binding agent shown in grey (6). There is a porous membrane (7) at the bottom of the container, and a porous membrane (8) at the top of the container in order to contain the agarose beads within the container. The bead sizes are shown highly magnified for illustration purposes. Each agarose layer will be composed of a different binding agent bound to the agarose beads. For example, in an affinity device composed of four agarose bead layers; the first layer may consist of immobilized "altered IgG"; the second layer may consist of immobilized "altered IgG" binding agent; the third layer may consist of immobilized TNF-alpha binding agent; and the fourth layer may consist of immobilized IL-1 binding agent. The agarose layers are separated by internal filters that have pores of sufficient dimension to allow plasma to circulate through the various layers before exiting from the device. Typically the composition of the binding layers will be: one binding layer composed of immobilized "altered IgG"; a second layer composed of immobilized "altered IgG" binding agent selected as either immobilized anti-"altered IgG" antibody, or immobilized rheumatoid factor, or immobilized anti-"altered IgG" aptamer; a third layer composed of immobilized anti-TNF-alpha binding agent selected from either immobilized anti-TNF-alpha antibody, or immobilized TNF receptor, or immobilized anti-TNF-alpha aptamer; and a fourth layer composed of immobilized anti-IL-1 binding agent selected from either immobilized anti-IL-1 antibody, or immobilized IL-1 receptor, or immobilized anti-IL-1 aptamer. It is obvious that the number and sequential arrangement of the agarose bead layers may be changed without affecting the novelty of this invention.

Figure 2:
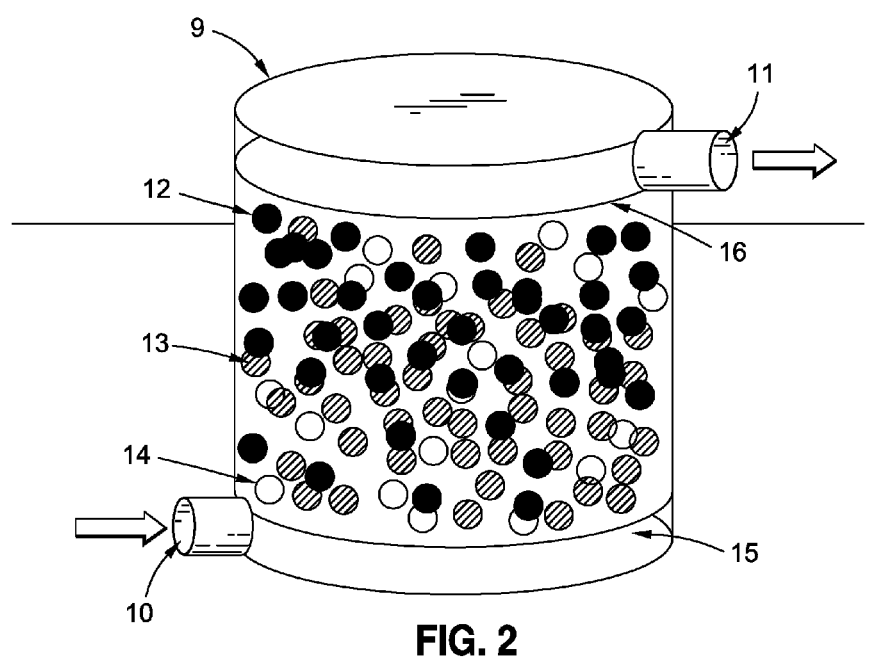
FIG. 2 is a schematic of a targeted affinity device using a mixed bed of immobilized binding agents.

In one embodiment of this invention the affinity device will contain a mixture of different immobilized binding agents bound to different agarose beads (FIG. 2). In the example shown in FIG. 2, the device consists of a rigid container (9) with an inlet orifice (10) and an outlet orifice (11). Within the container there is mixture of agarose beads coated with three different binding agents. Agarose beads coated with one type of binding agent are shown in black (12), those coated with a different binding agent are shown in grey (13) and those coated with yet another binding agent are shown in white (14). There is a porous membrane (15) at the bottom of the container, and a porous membrane (16) at the top of the container in order to contain the agarose beads within the container. The bead sizes are shown highly magnified for illustration purposes. Each agarose bead has a single species of binding agent fixed to its matrix. For example, a batch of "altered IgG" agarose beads is prepared; another batch of "altered IgG" binding agent agarose beads is prepared; another batch of TNF-alpha binding agent agarose beads is prepared; and another batch of IL-1 binding agent agarose beads is prepared. Typically, two or more batches of immobilized binding agents will be mixed and used in the affinity device. For example, in a mixed bed containing four different binding agents the mixture would be composed as follows: a batch of immobilized "altered IgG"; a second batch of immobilized "altered IgG" binding agent selected as either immobilized anti-"altered IgG" antibody, or immobilized rheumatoid factor, or immobilized anti-"altered IgG" aptamer; a third batch of immobilized anti-TNF-alpha binding agent selected from either immobilized anti-TNF-alpha antibody, or immobilized TNF receptor, or immobilized anti-TNF-alpha aptamer; and a fourth batch of immobilized anti-IL-1 binding agent selected from either immobilized anti-IL-1 antibody, or immobilized IL-1 receptor, or immobilized anti-IL-1 aptamer. It is obvious that one or more of the immobilized binding agents can be omitted and/or various permutations of the binding agents can be included in the mixed bed without affecting the novelty of this invention.

Description of Targeted Apheresis

The overall procedure for targeted apheresis is the same as that used in conventional apheresis. Briefly, blood from the patient is circulated extra-corporeally using standard apheresis equipment. The blood is separated into the cellular elements (red blood cells, white blood cells and platelets) and fluid (plasma) elements using differential centrifugation or a membrane filter. The separated plasma is then pumped through the affinity device where the pathogenic and pro-inflammatory elements are bound to the immobilized ligands and removed. The cleaned plasma then exits the affinity device and is mixed with the cellular blood elements and returned to the patient.

In one embodiment of the invention the plasma is circulated through an affinity device composed of two or more layers of immobilized binding agents. For example, in an affinity device composed of four binding layers; the first layer may consist of immobilized "altered IgG" agarose beads; the second layer may consist of immobilized anti-"altered IgG" agarose beads; the third layer may consist of immobilized TNF alpha binding agent agarose beads; and the fourth layer may consist of immobilized IL-1 binding agent agarose beads. When plasma passes through the first layer the circulating rheumatoid factors will bind to the immobilized "altered IgG" and be removed. The rheumatoid factors may be of the IgM, IgG or IgA class of immunoglobulin. At the same time circulating IgG:IgM immune complexes that have free binding sites remaining on the IgM molecule are also removed because these binding sites will bind to the immobilized "altered IgG". The plasma now enters the second layer where the immobilized anti-"altered IgG" binding agent will bind out circulating "altered IgG". At the same time any circulating IgG:IgG immune complexes are also removed by the immobilized anti-altered IgG binding agent which recognizes the IgG autoantibody in the immune complex as "altered IgG". The plasma now enters the third layer where the immobilized TNF-alpha binding agent will bind out the circulating TNF-alpha. The plasma now enters the fourth layer where the immobilized IL-1 binding agent will bind out the circulating IL-1. It is obvious that certain layers can be omitted and/or their sequential arrangement can be changed without affecting the novelty of this invention. The selection of the binding agents to be included in the various binding layers will determine which pathogenic and pro-inflammatory factors will be specifically removed.

In another embodiment of the invention the plasma is circulated through an affinity device composed of a mixed bed of different immobilized binding agents. For example, the mixed bed may contain immobilized "altered IgG" agarose beads, immobilized anti-"altered IgG" binding agarose beads, immobilized TNF-alpha binding agarose beads, and immobilized IL-1 binding agarose beads. When plasma enters the mixed bed of immobilized binding agents the circulating pathological and pro-inflammatory factors will be bound out by their respective immobilized binding agents. It is obvious that one or more of the immobilized binding agents can be omitted from inclusion within the mixed bed without affecting the novelty of this invention. The selection of the binding agents to be included in the mixed bed will determine which pathogenic and pro-inflammatory factors will be specifically removed.

There is one novel aspect of the mixed bed arrangement that is counter-intuitive to conventional thinking. This is to mix an immobilized antigen (i.e. "altered IgG" agarose) with its corresponding immobilized antibody (anti-"altered IgG" antibody agarose or rheumatoid factor agarose) because it would appear that these would neutralize each other and therefore hinder their ability to remove circulating rheumatoid factor and "altered IgG" from the patient's blood. By contrast, in this invention we teach that there will be no significant impairment of their binding efficiency for the following reasons: The ability of the immobilized antigen and immobilized antibody to react with each other is limited by their relative sizes compared to the size of the agarose beads. And because antigen:antibody bridging can only occur when the curved surfaces of the two agarose beads are in close approximation, the actual reaction area where bridging can occur is relatively small compared to the total surface area of the bead that will have many more active sites that cannot be bridged. Moreover, because of the porosity of the agarose beads there are yet many more sites where the reactants are immobilized on the surfaces of the internal pores where bridging obviously cannot occur. Further, when other immobilized binding agents such as TNF-alpha binding agarose beads and/or IL-1 binding agarose beads are also included in the mixed bed these unrelated agarose beads will physically block some of the immobilized antigen beads from coming into close contact with their corresponding immobilized antibody beads thus further reducing the number of areas where bridging can occur. The net result is that it is possible to mix immobilized antigen beads with their corresponding immobilized antibody beads and have no significant impairment on their ability to simultaneously and selectively remove rheumatoid factors, immune complexes and "altered IgG" from the blood of patients with RA.

The same arguments apply when immobilized anti-"altered IgG" aptamer is used instead of immobilized anti-"altered IgG" antibody. To summarize, bridging between the immobilized "altered IgG" and the immobilized aptamer will be limited because of the size and curvature of the agarose beads; the reactants are also immobilized within the internal pores of their respective agarose beads where bridging cannot occur; and including unrelated agarose beads in the mixed bed will physically block the immobilized altered IgG beads from coming into close contact with their corresponding immobilized anti-altered IgG aptamer beads. The net result is that it is possible to mix immobilized "altered IgG" beads with the corresponding immobilized anti-"altered IgG" aptamer beads and have no significant impairment on their ability to simultaneously and selectively remove rheumatoid factors, immune complexes and altered IgG from the blood of patients with RA.

Terminology

In this invention the term "antibody" is used to mean the whole antibody molecule, and/or the Fab or F(ab)2 binding fragments of the antibody molecule.

In this invention the term "aptamer" is used to mean either of the synthetic oligonucleotides ssDNA and/or ssRNA.

In this invention the term "Tumor Necrosis Factor Receptor" (TNF-R) is used to include both the TNF-R1 (or p55) and TNF-R2 (or p75) receptors; and to mean the whole TNF-R1 or TNF-R2 receptor moieties, and/or the binding domains of the TNF-R1 or TNF-R2 receptors.

In this invention the term 'Interleukin-1 Receptor" (IL-1) is used to mean the whole IL-1 receptor moiety and/or the binding domains of the IL-1 receptor.

In this invention the term "cross-linked agarose beads" is used to mean spherical porous agarose beads in which the porosity and gel strength of the bead is related to its agarose concentration. The agarose concentration of the beads includes any selection within the range of from one percent cross-linked agarose to ten percent cross-linked agarose.

Single use and Multiple use Affinity Devices.

The targeted apheresis affinity device may be employed as a single use disposable device or it may be regenerated and used multiple times. To regenerate the device an elution buffer solution is passed through the device to release the pathogenic ligands bound to the immobilized matrix. For example, an elution buffer such as glycine-HCl buffer pH 2 will dissociate antigen:antibody bonds. The unbound ligand is washed out of the device and the regenerated agarose matrix is then washed and stored in physiological buffer such as phosphate buffered saline pH 7.2 with preservatives. Other eluting buffers and storage buffers are known to those skilled in the art and are within the scope of this invention. Typically, the affinity device is stored in the cold at 2-8 C.

Targeted Apheresis Therapy of Other Autoimmune Diseases and Immune Disorders

It will be obvious to one of ordinary skill from the principles and methods enumerated here that targeted apheresis can be applied to a wide variety of autoimmune and inflammatory disorders.

In one embodiment of this invention targeted apheresis is used to treat patients with SLE. Patients with SLE have autoantibodies to nuclear antigens. These antinuclear antibodies are believed to cause kidney damage either by binding to the glomeruli cells in the kidney and/or forming immune complexes which are then deposited within the glomerulus. It would be desirable to develop an apheresis method to remove these autoantibodies and/or immune complexes from the blood and thus prevent them from causing damage to the kidney and other tissues. Patients with SLE also have pro-inflammatory cytokines such as tumor necrosis factor-alpha (TNF-alpha) and interleukin-1 (IL-1) that may stimulate the autoimmune response and exacerbate disease symptoms. It would be desirable to develop an apheresis method that would also remove these pro-inflammatory elements and ameliorate disease symptoms.

SLE patients can be treated using the single affinity device of this invention to simultaneously and selectively remove multiple pathogenic and pro-inflammatory factors from their blood. The affinity device can be configured as multiple layers of immobilized binding agents specific for the pathogenic and pro-inflammatory elements associated with SLE (figure1) or the affinity device can be configured as a mixed bed of different immobilized binding agents specific for the pathogenic and pro-inflammatory elements associated with SLE (FIG. 2). For example, to remove antinuclear antibodies the immobilized binding agent is a nuclear extract chemically conjugated to cross-linked agarose beads; to remove immune complexes the immobilized binding agent is selected from either immobilized anti-"altered IgG" antibody, or immobilized rheumatoid factor, or immobilized anti-"altered IgG" aptamer; to remove TNF-alpha the immobilized binding agent selected from either immobilized anti-TNF-alpha antibody, or immobilized TNF receptor, or immobilized anti-TNF-alpha aptamer; to remove IL-1 the immobilized binding agent selected from either immobilized anti-IL-1 antibody, or immobilized IL-1 receptor, or immobilized anti-IL-1 aptamer. It is obvious that the number and disposition of the various binding agents may be changed without affecting the novelty of this invention.

In one embodiment of this invention targeted apheresis is used to treat patients with myasthenia gravis. Patients with MG have an autoantibody that appears to block the binding of the hormone acetylcholine to acetylcholine receptors of the neuromuscular junction of the muscle cell. It would be desirable to remove this autoantibody using targeted apheresis and alleviate the disease symptoms of MG. To remove the autoantibody the affinity device will contain immobilized recombinant human acetylcholine receptor protein or an immobilized receptor mimetic peptide or an immobilized receptor mimetic aptamer. The methods for preparing recombinant acetylcholine receptor protein or receptor mimetic peptides or receptor mimetic aptamers are known to those skilled in the art. As described earlier the affinity device can contain additional specific immobilized binding agents to also remove pro-inflammatory cytokines such as TNF-alpha and IL-1 from the blood.

In one embodiment of this invention targeted apheresis is used to treat patients with osteoarthritis (OA). Although osteoarthritis is not classified as an autoimmune disease patients with OA often have features in common with RA. For example, patients with OA often have elevated levels of rheumatoid factor and/or TNF-alpha and/or IL-1 in their synovial fluid and in their blood. Removal of these factors using targeted apheresis as described earlier for RA may alleviate some of the symptoms of OA.

The above descriptions and illustrations are given by way of example, and not limitation. Given the above disclosures, one skilled in the art could devise variations and applications that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments of the invention

What is claimed is:

1. A method for treating an autoimmune or inflammatory disorder in a patient using targeted apheresis, the method comprising the steps of:
   a) providing an apheresis device comprising:
      one or more first immobilized binding agent for binding altered IgG and being selected from: anti-altered IgG antibody, anti-altered IgG aptamer, and rheumatoid factor; and
      one or more second immobilized binding agent for binding at least one other antigen, the second immobilized binding agent being selected from: altered IgG, anti-TNF-alpha antibody, anti-TNF-alpha aptamer, TNF receptor, IL-1, anti-IL-1 antibody, IL-1 receptor, anti-IL-1 aptamer, nuclear extract, acetylcholine receptor protein, acetylcholine receptor mimetic peptide, acetylcholine receptor mimetic aptamer; and
   b) passing the patient's plasma through the apheresis device to bind altered IgG and the at least one other antigen present in the patient's plasma.

2. The method of claim 1, wherein the autoimmune or inflammatory disorder being treated is rheumatoid arthritis.

3. The method of claim 1, wherein the autoimmune or inflammatory disorder being treated is systemic lupus erythematosus.

4. The method of claim 1, wherein the autoimmune or inflammatory disorder being treated is myasthenia gravis.

5. The method of claim 1, wherein the autoimmune or inflammatory disorder being treated is osteoarthritis.

6. The method of claim 1, wherein one of the one or more second immobilized binding agents selected is altered IgG, and the altered IgG is prepared from heat-denatured purified human IgG.

7. The method of claim 1, wherein one of the one or more first immobilized binding agent selected is anti-altered IgG antibody, and wherein the anti-altered IgG antibody is a monoclonal antibody and/or a polyclonal antibody.

8. The method of claim 1, wherein the first immobilized binding agent is anti-altered IgG antibody and comprises the whole anti-altered IgG antibody molecules.

9. The method of claim 1, wherein the first immobilized binding agent is anti-altered IgG antibody and comprises Fab or F(ab)2 binding fragments of anti-altered IgG antibody molecules.

10. The apheresis device of claim 9, wherein the insoluble support matrix comprises agarose beads.

11. The apheresis device of claim 9, wherein the insoluble support matrix comprises two or more layers of agarose beads.

12. An apheresis device for the treatment of an autoimmune or inflammatory disorder using targeted apheresis, the apheresis device comprising:
an affinity column having an inlet and an outlet;
an insoluble support matrix contained within the affinity column;
one or more first immobilized binding agents chemically coupled to the insoluble support matrix for binding altered IgG, the first immobilized binding agent being selected from: anti-altered IgG antibody, anti-altered IgG aptamer, and rheumatoid factor; and
one or more second immobilized binding agents chemically coupled to the insoluble support matrix for binding at least one other antigen, the second immobilized binding agent being selected from: altered IgG, anti-TNF-alpha antibody, anti-TNF-alpha aptamer, TNF receptor, IL-1, anti-IL-1 antibody, IL-1 receptor, anti-IL-1 aptamer, nuclear extract, acetylcholine receptor protein, acetylcholine receptor mimetic peptide, acetylcholine receptor mimetic aptamer.

13. The apheresis device of claim 12, wherein the first immobilized binding agent is anti-altered IgG antibody and comprises whole anti-altered IgG antibody molecules.

14. The method of claim 12, wherein the first immobilized binding agent is anti-altered IgG antibody and comprises Fab or F(ab)2 binding fragments of anti-altered IgG antibody molecules.

15. The device of claim 14, wherein the first immobilized binding agent is anti-altered IgG antibody and comprises whole anti-altered IgG antibody molecules.

16. The method of claim 14, wherein the first immobilized binding agent is anti-altered IgG antibody and comprises Fab or F(ab)2 binding fragments of anti-altered IgG antibody molecules.

17. A method for treating an autoimmune or inflammatory disorder in a patient using targeted apheresis, the method comprising the steps of:
a) providing an apheresis device containing one or more first immobilized binding agent for binding altered IgG, the first immobilized binding agent being selected from: anti-altered IgG antibody, anti-altered IgG aptamer, and rheumatoid factor; and
b) passing the patient's plasma through the apheresis device to bind altered IgG present in the patient's plasma.

18. The method of claim 17, wherein the first immobilized binding agent is anti-altered IgG antibody and comprises whole anti-altered IgG antibody molecules.

19. The method of claim 17, wherein the first immobilized binding agent is anti-altered IgG antibody and comprises Fab or F(ab)2 binding fragments of anti-altered IgG antibody molecules.

20. An apheresis device for the treatment of an autoimmune or inflammatory disorder using targeted apheresis, the apheresis device comprising:
an affinity column having an inlet and an outlet;
an insoluble support matrix contained within the affinity column; and
one or more first immobilized binding agents chemically coupled to the insoluble support matrix for binding altered IgG, the first immobilized binding agent being selected from: anti-altered IgG antibody, anti-altered IgG aptamer, and rheumatoid factor.

* * * * *